US006194570B1

(12) United States Patent
Ollivier et al.

(10) Patent No.: US 6,194,570 B1
(45) Date of Patent: Feb. 27, 2001

(54) PROCESS FOR THE PREPARATION OF LAURYLLACTAM BY PHOTONITROSATION OF CYCLODODECANE AND BECKMANN REARRANGEMENT IN THE PRESENCE OF METHANESULPHONIC ACID

(75) Inventors: Jean Ollivier, Arudy; Damien Drutel, Lyons, both of (FR)

(73) Assignee: Atofina, Paris la Defense Cedex (FR)

( * ) Notice: Subject to any disclaimer, the term of this patent is extended or adjusted under 35 U.S.C. 154(b) by 0 days.

(21) Appl. No.: 09/400,996

(22) Filed: Sep. 21, 1999

(30) Foreign Application Priority Data

Sep. 21, 1998 (FR) .................................................. 98 11734

(51) Int. Cl.⁷ .................................................. C07D 227/08
(52) U.S. Cl. ........................................... 540/464; 564/253
(58) Field of Search .............................. 540/464; 564/253

(56) References Cited

U.S. PATENT DOCUMENTS 2,721,199 * 10/1955 Huber ................................ 260/239.3
4,211,700 * 7/1980 Michel et al. ..................... 260/239.3
4,689,412 * 8/1987 Rademacher et al. ............... 540/464
5,719,316 * 2/1998 Ollivier .............................. 564/253

FOREIGN PATENT DOCUMENTS 1.335.822    12/1963  (FR) .
2 417 501     9/1979  (FR) .
WO 99/01424 *  1/1999  (WO) .

* cited by examiner

Primary Examiner—Mukund J. Shah
Assistant Examiner—Bruck Kifle
(74) Attorney, Agent, or Firm—Millen, White, Zelano & Branigan, P.C.

(57) ABSTRACT

A process for the preparation of lauryllactam comprises:
(a) photochemically reacting cyclododecane solubilized in an organic solvent, a nitrosing agent and hydrogen chloride in the presence of an acid in order to form cyclododecanone oxime, and
(b) subjecting said oxime to a Beckmann rearrangement in the presence of an acid, said process being characterized in that the acid used comprises methanesulphonic acid.

20 Claims, No Drawings

PROCESS FOR THE PREPARATION OF LAURYLLACTAM BY PHOTONITROSATION OF CYCLODODECANE AND BECKMANN REARRANGEMENT IN THE PRESENCE OF METHANESULPHONIC ACID

CROSS-REFERENCE TO RELATED APPLICATION

This application is related to a concurrently filed and commonly owned application entitled "Process for the Preparation of Lactams from the Corresponding Cycloalkanone Oximes", attorney docket ATOCM-156 by OLLIVIER, based on French application 98/11733 filed on Sep. 21, 1998, respectively.

FIELD OF THE INVENTION

DESCRIPTION

The present invention relates to the preparation of lauryllactam which constitutes the basic monomer of polyamide 12. More precisely, it relates to a process for the preparation of lauryllactam from cyclododecane in which the photonitrosation and Beckmann rearrangement steps are carried out in the presence of methanesulphonic acid.

BACKGROUND OF THE INVENTION

Lauryllactam is widely used for the preparation of polyamide 12. Its production on an industrial scale is well known [see for example "Precédé de Pétrochimie" (Petrochemical Process), Volume 2, pp. 316–322, published by Technip, 1986]. It is possible, for example, to manufacture lauryllactam from cyclododecane (HULS and Ato Chimie process), from cyclododecanone (UBE process) or alternatively from cyclododecatriene monoozonide (Snia Viscosa process).

In the process developed by Ato Chimie, the lauryllactam is obtained in two stages:
in the first stage, cyclododecanone oxime hydrochloride is formed by photonitrosation of cyclododecane solubilized in a chlorinated solvent according to the following reaction:

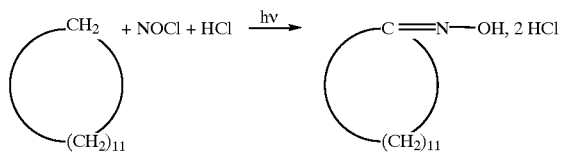

and, in the second stage, the reaction product is subjected to a Beckmann rearrangement in the presence of sulphuric acid:

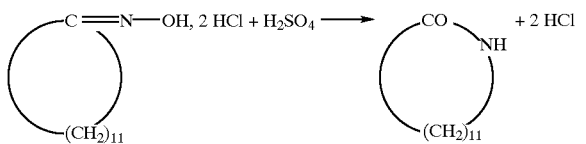

The cyclododecanone oxime hydrochloride formed during the photonitrosation is solid and very stable, and it becomes deposited on the walls of the irradiation lamps in contact with the reaction medium. Under the effect of light, the deposit is gradually converted to a tarry substance which, in the relatively long term, causes the termination of the photochemical reaction.

To overcome this difficulty, it is known to add sulphuric acid to the reaction mixture (see for example FR-B-1,335,822 and FR-B-1,553,268). In this manner, the sulphuric acid extracts the cyclododecanone oxime hydrochloride as it is formed. Having avoided any risk of deposition, it becomes possible to carry out the reaction continuously.

However, the use of sulphuric acid has disadvantages, both at the level of the first and second stage of the process.

In the photonitrosation stage, sulphuric acid:
colours the reaction medium, thus causing a loss in the number of photons essential for the reaction,
disperses with difficulty in the reaction medium because of its high viscosity and its ionized character,
reacts with nitrosyl chloride to form nitrosyl acid sulphate, which sulphate contributes towards degrading the oxime hydrochloride,
hydrolyses the oxime hydrochloride to cyclododecanone and hydroxylamine, and
reacts with the nitrosing agent, which has the effect of retarding the onset of the reaction and, consequently, of reducing production.

In the Beckmann rearrangement stage, the reaction is carried out at a high temperature, greater than 135° C. Consequently, the disadvantages linked to the use of sulphuric acid are as follows:
in the presence of organic compounds, sulphuric acid decomposes, releasing undesirable sulphur dioxide whose content increases during recycling of the organic phase containing the unreacted cyclododecane,
a portion of the oxime is hydrolysed to the corresponding ketone,
a portion of the lactam is hydrolysed to the corresponding amino acid which, under the process conditions, cannot be recovered and profitably exploited, and
sulphuric acid is capable of decomposing the chlorinated reaction solvent carried by the acidic phase to phosgene which is toxic for humans.

Furthermore, all the sulphuric acid-containing effluents generated by the industrial process can only be recycled at the cost of a long, difficult and costly treatment because it is in particular necessary to use steps for concentrating the acid and for removing organic compounds.

SUMMARY OF THE INVENTION

It has now been found that the abovementioned disadvantages can be overcome by advantageously replacing sulphuric acid with methanesulphonic acid, without affecting the overall yield of the process as a result.

The subject of the invention is therefore a new process for the preparation of lauryllactam which consists in:
a-photochemically reacting cyclododecane solubilized in an organic solvent, a nitrosing agent and hydrogen chloride in the presence of an acid in order to form cyclododecanone oxime, and
b-subjecting the said oxime to a Beckmann rearrangement in the presence of an acid, the said process being characterized in that the acid used is methanesulphonic acid.

The process according to the invention will be understood more clearly in the light of the following description.
Photonitrosation Stage To carry out the reaction, the process is generally carried out in a reactor into which a mixture comprising cyclododecane in solution in an organic solvent and methanesulphonic acid, hydrogen chloride and a nitrosing agent is introduced, and the mixture is irradiated with light.

The cyclododecane may be obtained according to methods known to persons skilled in the art, for example by cyclotrimerization of butadiene and hydrogenation of the cyclotriene formed.

The cyclododecane is solubilized in an appropriate organic solvent, for example a chlorinated hydrocarbon such as chloroform or chlorobenzene. The content of cyclododecane in the solvent is generally between 0.1 and 40% by weight, and preferably 20 and 30% by weight.

The methanesulphonic acid is generally used in the form of an aqueous solution whose content may vary between 70 and 90% by weight, preferably 95 and 99% by weight.

The methanesulphonic acid used represents in general 6 to 12% of the volume of the reaction medium, and preferably 8 to 9%.

The nitrosing agent is chosen from nitrosyl chloride, a mixture of nitric oxide and chlorine, and compounds capable of forming nitrosyl chloride in the reaction medium, for example alkyl nitrites which react with hydrogen chloride. Nitrosyl chloride is preferably used.

The addition of the nitrosing agent is regulated such that its concentration in the reaction medium is between 0.1 and 25 g/l, and preferably 1 and 2 g/l.

The hydrogen chloride is introduced in the form of an anhydrous gas, in excess relative to the nitrosing agent. Preferably, it is used at saturation of the solution of cyclododecane in the solvent.

The irradiation is carried out by means of one or more mercury or sodium vapour lamps emitting radiation of wavelength between 500 and 700 nm, and preferably 565 and 620 nm.

The reaction is carried out at a temperature of between −20 and +40° C., and preferably +10 and +20° C.

The procedure is generally carried out with vigorous stirring. In the present invention, the expression "vigorous stirring" is understood to mean stirring such that the reaction volume is renewed at least 100 times per hour. It is possible, for that, to use any stirring means, for example one or more turbines or recirculating pumps.

The photonitrosation is generally carried out in a reactor which can function batchwise or continuously. Continuous operation is preferred.

After irradiation, the reaction mixture is separated after settling out and the cyclododecanone oxime is recovered in the acidic phase. The content of cyclododecanone oxime in the acidic phase may vary to a large degree. However, for reasons linked to industrial conditions, an oxime content of between 10 and 40% by weight, and better still 25 and 35%, is preferred.

Beckmann Rearrangement Stage

This stage is generally carried out in a reactor operating at high temperature and with vigorous stirring.

The cyclododecanone oxime obtained at the end of the preceding photonitrosation stage is generally introduced as it is into the reactor. For obvious safety reasons linked to the very high exothermicity of the reaction, it is preferable to introduce the oxime solution into a reactor which contains a suitable volume of methanesulphonic acid maintained at the temperature required to carry out the rearrangement. This volume can, as known to persons skilled in the art, vary to a large degree depending on whether the reaction is carried out continuously or batchwise.

The process is generally carried out at a temperature of between 120 and 180° C., preferably 140 and 160° C., and for a period such that the residence time in the reactor varies from 2 minutes to 1 hour, preferably 15 to 30 minutes.

The rearrangement is carried out under conditions of vigorous stirring as defined above.

A solution of lauryllactam in methanesulphonic acid is thus recovered. This solution is generally subjected to one or more separation and purification treatments in order to obtain lauryllactam having a purity greater than 99%.

The methanesulphonic acid recovered can be easily purified, for example by simple distillation, and reintroduced into the process.

The following examples make it possible to illustrate the invention.

EXAMPLE a-Photonitrosation

Into a two-litre reactor (working volume) equipped with a sodium vapour lamp having a power rating of 400 watt and emitting a radiation maximum in the vicinity of 595 nm, there are introduced, continuously, a solution of cyclododecane in chloroform (450 g/l; 1 l/h), anhydrous gaseous hydrochloric acid to saturation, nitrosyl chloride and an aqueous solution of methanesulphonic acid at 90%. The flow rate of nitrosyl chloride is regulated such that the concentration in the reactor is maintained at 2 g/l of reaction medium. The volume of the solution of methanesulphonic acid introduced represents 10% of the total volume of the reaction medium.

The gaseous effluents originating from the reactor are directed to a condenser (recovery of the solvent) and a bubbler containing a solution of sodium hydroxide (trapping of the hydrochloric acid).

The reaction medium is drawn off continuously at the rate of about 1.1 l/h and separated after settling out. In a stationary regime, 0.52 mol/h of cyclododecanone oxime hydrochloride and 0.00867 mol/h of chlorocyclododecanone oxime hydrochloride are recovered in the aqueous phase, and 0.0208 mol/h of monochlorocyclododecane and $8.25 \times 10^{-4}$ mol/h of dichlorocyclododecane in the organic phase.

The number of moles of cyclododecane converted per hour is equal to 0.55. The molar selectivity in relation to cyclododecanone oxime hydrochloride is equal to 0.928 calculated on the basis of unreacted cyclododecane.

b-Beckmann Rearrangement 231 g of the acidic phase separated after settling out in stage a- which contains 31% by weight of cyclododecanone oxime (0.363 mol) are added, over 1 hour, to 100 g of methanesulphonic acid maintained at 120° C. and with stirring. The reaction medium is heated at 135–140° C. for 1 hour in order to complete the rearrangement.

Water (30% by weight) is added to the reaction medium so as to cause the lauryllactam to precipitate and the medium is filtered. The filtration cake is dissolved in a cyclohexane/toluene (50/50 v/v) mixture and recrystallized. The operation is repeated twice.

70.9 g of lauryllactam are thus recovered (yield: 99%).

The total yield of lauryllactam synthesis is equal to 91.8% (0.928×99%).

COMPARATIVE EXAMPLE

The process is carried out under the conditions of the preceding example, modified in that methanesulphonic acid is replaced with sulphuric acid.

a-Photoni Trosation

In a stationary regime, 0.433 mol/h of cyclododecanone oxime hydrochloride and 0.011 mol/h of chlorocyclododecanone oxime hydrochloride are recovered in the aqueous phase, and 0.016 mol/h of monochlorocyclododecane and $5 \times 10^{-4}$ mol/h of dichlorocyclododecane in the organic phase. The number of moles of cyclododecane converted per hour is equal to 0.495.

The molar selectivity in relation to cyclododecanone oxime hydrochloride is equal to 0.875 calculated on the basis of the unreacted cyclododecane.

b-Beckmann Rearrangement 250 g of the acidic phase separated after settling out of stage a- which contains 30% by weight of cyclododecanone oxime (0.38 mol) are added, over one hour, to 100 g of sulphuric acid at 98% maintained at 120° C. and with stirring. After 1 hour at 135–140° C., the reaction medium contains, in addition to lauryllactam, 1.125 g of cyclododecanone, 0.75 g of 12-aminododecanoic acid and about 500 ppm of sulphur dioxide. The rearrangement gases contain sulphur dioxide (for a quantity corresponding to the decomposition of about 1% of the starting sulphuric acid) and several tens of ppm of phosgene.

After extraction under the conditions of Example 1, 73.12 g of lauryllactam are recovered (yield: 97.5%).

The total yield of lauryllactam synthesis is equal to 85%.

Whereas the acid employed is advantageously methanesulphonic acid, it is also contemplated that the methanesulphonic acid may be mixed with other acids so long as the net effect is not to lose all the beneficial effects associated with the use of methanesulphonic acid.

The preceding examples can be repeated with similar success by substituting the generically or specifically described reactants and/or operating conditions of this invention for those used in the preceding examples. Also, the preceding specific embodiments are to be construed as merely illustrative, and not limitative of the remainder of the disclosure in any way whatsoever.

The entire disclosure of all applications, patents and publications, cited above and below, and of corresponding French application 98/11734, are hereby incorporated by reference.

From the foregoing description, one skilled in the art can easily ascertain the essential characteristics of this invention, and without departing from the spirit and scope thereof, can make various changes and modifications of the invention to adapt it to various usages and conditions.

What is claimed is:

1. In a process for preparing lauryllactam comprising:
   (a) photochemically reacting cyclododecane solubilized in an organic solvent, a nitrosing agent and hydrogen chloride in the presence of acid in order to form cyclododecanone oxime, and
   (b) subjecting said oxime to a Beckmann rearrangement in the presence of acid, the improvement wherein the acid consists essentially of methanesulphonic acid.

2. A process according to claim 1, wherein the organic solvent consists essentially of a chlorinated hydrocarbon.

3. A process according to claim 2, wherein the solvent consists essentially of chloroform or chlorobenzene.

4. A process according to claim 1, wherein the methanesulphonic acid in stage (b) represents 6 to 12% of the volume of the reaction medium.

5. A process according to claim 4, wherein the methanesulphonic acid represents 8 to 9% of the reaction volume.

6. A process according to claim 1, wherein the oxime of stage (b) is in the form of a solution containing 10 to 40% by weight of oxime in methanesulphonic acid.

7. A process according to claim 6, wherein the solution contains 25 to 35% by weight of oxime.

8. A process according to claim 2, wherein the methanesulphonic acid in stage (a) represents 6 to 12% of the volume of the reaction medium.

9. A process according to claim 8, wherein the methanesulphonic acid represents 8 to 9% of the reaction volume.

10. A process according to claim 2, wherein the oxime of stage (b) is in the form of a solution containing 10 to 40% by weight of oxime in methanesulphonic acid.

11. A process according to claim 8, wherein the oxime of stage (b) is in the form of a solution containing 10 to 40% by weight of oxime in methanesulphonic acid.

12. A process according to claim 9, wherein the oxime of stage (b) is in the form of a solution containing 10 to 40% by weight of oxime in methanesulphonic acid.

13. A process according to claim 10, wherein the solution contains 25 to 35% by weight of oxime.

14. A process according to claim 11, wherein the solution contains 25 to 35% by weight of oxime.

15. A process according to claim 12, wherein the solution contains 25 to 35% by weight of oxime.

16. In a process for preparing lauryllactam, the step of photochemically reacting cyclododecane solubilized in an organic solvent, a nitrosing agent and hydrogen chloride in the presence of acid in order to form cyclododecanone oxime, the improvement wherein the acid consists essentially of methanesulphonic acid.

17. A process according to claim 16, wherein the organic solvent consists essentially of a chlorinated hydrocarbon.

18. A process according to claim 17, wherein the solvent consists essentially of chloroform or chlorobenzene.

19. A process according to claim 16, wherein the methanesulphonic acid in stage (a) represents 6 to 12% of the volume of the reaction medium.

20. In a process for preparing cyclododecanone oxime, the step of photochemically reacting cyclododecane solubilized in an organic solvent, a nitrosing agent and hydrogen chloride in the presence of acid in order to form cyclododecanone oxime, the improvement wherein said acid consists essentially of methanesulphonic acid.

* * * * *